(12) United States Patent
Ignatyev et al.

(10) Patent No.: US 7,576,242 B2
(45) Date of Patent: Aug. 18, 2009

(54) PROCESS FOR THE PREPARATION OF ORGANIC SALTS CONTAINING BIS(PERFLUOROALKYL) PHOSPHINATE ANIONS

(75) Inventors: Nikolai Mykola Ignatyev, Duisburg (DE); Urs Welz-Biermann, Heppenheim (DE); Helge Willner, Muhlheim/Ruhr (DE); Andriy Kucheryna, Wuppertal (DE)

(73) Assignee: Merck Patent GmbH, Darmstadt (DE)

( * ) Notice: Subject to any disclaimer, the term of this patent is extended or adjusted under 35 U.S.C. 154(b) by 232 days.

(21) Appl. No.: 10/579,555

(22) PCT Filed: Oct. 26, 2004

(86) PCT No.: PCT/EP2004/012074

§ 371 (c)(1),
(2), (4) Date: May 16, 2006

(87) PCT Pub. No.: WO2005/049555

PCT Pub. Date: Jun. 2, 2005

(65) Prior Publication Data

US 2007/0128515 A1    Jun. 7, 2007

(30) Foreign Application Priority Data

Nov. 17, 2003   (DE)   ................. 103 53 758

(51) Int. Cl.
*C07F 9/02* (2006.01)
(52) U.S. Cl. .......................................... 568/16
(58) Field of Classification Search ............ 568/16
See application file for complete search history.

(56) References Cited

FOREIGN PATENT DOCUMENTS

WO    WO 03087110    10/2003

OTHER PUBLICATIONS

Pavlenko et al., 1989, CAS: 111:194893.*
Pavlenko N.V. et al: Esters of bis(perfluoroalkyl)phosphinic acids, (Rf)2P(0)OR, are of interest as biologically active compounds, alkylating agents and surfactants: J. Gen. Chem. USSR, Bd. 59, 1989, XP002104254.

* cited by examiner

*Primary Examiner*—Rei-tsang Shiao
(74) *Attorney, Agent, or Firm*—Millen, White, Zelano, Branigan, P.C.

(57) ABSTRACT

The invention relates to a method for the production of organic salts containing bis(perfluoroalkyl)phosphinate anions. According to said method, a tris(perfluoroalkyl)phosphine oxide is reacted with an alcohol and an organic base, which is stronger than the alcohol. The invention also relates to the salts which are produced according to said method and to the use thereof as ionic liquids.

11 Claims, No Drawings

PROCESS FOR THE PREPARATION OF ORGANIC SALTS CONTAINING BIS(PERFLUOROALKYL) PHOSPHINATE ANIONS

The present invention relates to a process for the preparation of organic salts containing bis(perfluoroalkyl)phosphinate anions, and to the salts prepared by this process and to the use thereof as ionic liquids.

Quaternary ammonium and phosphonium salts are typically prepared by alkylation of amines or phosphines. To this end, use is made of various alkylating agents, such as, for example, alkyl halides, alkyl sulfates, alkyl triflates, inter alia. This process can also be used for the synthesis of salts containing heterocyclic cations. Disadvantages in this process are the high costs of the alkylating agent, the toxicity of these alkylating agents (dimethyl sulfate, for example, is highly toxic). Furthermore, only salts containing certain anions are obtainable via this process. In order to obtain salts containing other anions, an ion exchange by reaction of the salt with a Brönsted acid or a metal salt is necessary as an additional step. This makes the synthesis of organic salts containing certain anions very expensive.

In recent years, the interest in organic salts which have a very low melting point has grown. These compounds, owing to their low melting point, are increasingly being used as ionic liquids, as confirmed by some review articles in recent years (P. Wasserscheid, W. Keim, "Ionische Flüssigkeiten—neue Lösungen für die Übergangsmetallkatalyse" [Ionic Liquids—Novel Solutions for Transition-Metal Catalysis], Angew. Chem. 112 (2000) pp. 3926-3945; R. Sheldon, "Catalytic reactions in ionic liquids", Chem. Commun. 2001, pp. 2399-2407; M. J. Earle, K. R. Sheldon, "Ionic liquids. Green solvent for the future", Pure Appl. Chem. 72, No. 7 (1999), pp. 1391-1398; T. Welton, "Room temperature ionic liquids of alkylimidazolium cations and fluoroanions", J. of Fluorine Chem. 105 (2000) pp. 221-227). The term ionic liquid here implies that the compound is liquid at room temperature or at relatively low temperatures. In addition, it contains an organic cation, such as, for example, tetraalkylammonium, tetraalkylphosphonium, N-alkylpyridinium, 1,3-dialkylimidazolium and trialkylsulfonium cations, and a usually inorganic anion, such as, for example, $BF_4^-$, $PF_6^-$, $SbF_6^-$, $NO_3^-$, $CF_3SO_3^-$, $(CF_3SO_2)_2N^-$, $ArSO_3^-$, $CF_3CO_2^-$, $CH_3CO_2^-$, $Al_2Cl_7^-$.

The properties of the ionic liquids, such as, for example, the melting point, the thermal and electrochemical stability and the viscosity, are strongly influenced by the nature of the anion and of the cation. The polarity and hydrophilicity or lipophilicity can be adjusted through the choice of a suitable cation/anion pair. Each new anion and each new cation opens up further possibilities for tuning the properties of ionic liquids.

For practical use of ionic liquids, the economic efficiency, i.e. the price, is crucial. And judged by this factor, i.e. owing to their very high production costs, the ionic liquids known at present are not comparable with normal organic solvents. The development of novel processes which reduce the production costs of ionic liquids is therefore very important.

A process for the preparation of bis(perfluoroalkyl)phosphinic acid has recently been developed (DE 102 169 97). The neutralisation of these acids using organic bases, for example tetrabutylammonium hydroxide, results in the formation of the corresponding salts. Bis(perfluoroalkyl)phosphinic acid can furthermore be used for the conversion of organic chlorides into organic salts containing a bis(perfluoroalkyl)phosphinate anion with liberation of HCl. However, the synthesis of the corresponding chlorides (or bromides) via the alkylation process described above or the use of expensive alkylammonium or alkylphosphonium hydroxides is also necessary first here.

The reaction of tris(heptafluoropropyl)phosphine oxide with methanol, which results in the formation of dimethyl ether and bis(heptafluoropropyl)phosphinic acid, is known from the prior art (N. V. Pavlenko, et al., J, Gen. Chem. USSR (Engl. Transl.), 59, No. 3 (1989) pp. 474-476). The formation of this product was explained through the intermediate formation of the dimethyl ester of bis(heptafluoropropyl)phosphinic acid, which then alkylates the starting material methanol to give dimethyl ether.

The object of the present invention is to indicate an industrial and economically advantageous process for the preparation of salts containing bis(perfluoroalkyl)phosphinate anions which does not have the disadvantages of the prior art. In particular, the object of the present invention is to provide a process which has good yields and is simpler and less expensive than the processes known from the prior art.

This object is achieved in accordance with the invention by the characterising features of the main claim and the coordinated claims.

The invention is distinguished by the fact that tris(perfluoroalkyl)phosphine oxide forms the corresponding salt containing a bis(perfluoroalkyl)phosphinate anion in good yields by simple reaction with an alcohol and an organic base which is more strongly basic than the alcohol.

The bis(perfluoroalkyl)phosphinate anion can be represented by the formula $[(R^F)_2P(O)O]^-$, where $R^F$ in each case, independently of one another, denotes a perfluoroalkyl group, as described below.

Tris(perfluoroalkyl)phosphine oxide can be described by the formula $[(R^F)_3P=O]$, where $R^F$ in each case, independently of one another, denotes a perfluoroalkyl group, as described below.

The presence of a stronger base than the alcohol suppresses the undesired formation of the dialkyl ether, and the corresponding organic salts containing the bis(perfluoroalkyl)phosphinate anion are formed.

The monohydroperfluoroalkanes formed as by-product in the process according to the invention are likewise valuable substances. They can be isolated and used for various applications, such as, for example, as indicated in DE 102 16 995.

In the process according to the invention, virtually no superfluous substances which would have to be disposed of are therefore formed. Furthermore, owing to the starting materials used and the single reaction step, the process according to the invention can be carried out inexpensively.

The process according to the invention advantageously enables the preparation of compounds containing a bis(perfluoroalkyl)phosphinate anion in only a single process step. In addition, requisite starting materials for the newly introduced alkyl group of the cation are not expensive alkylating agents, but instead cheap alcohols.

The process according to the invention for the preparation of organic salts containing bis(perfluoroalkyl)phosphinate anions thus comprises at least the reaction of a tris(perfluoroalkyl)phosphine oxide with an alcohol and an organic base which is more strongly basic than the alcohol.

In a preferred variant of the process according to the invention, the organic base employed is a compound of the general formula (1)

or of the general formula (2)

in which:

X denotes

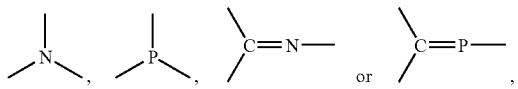

Y denotes —O—, —S—, —Se—, —C(=O)—, —C(=S)— or —C(=Se)—,

R denotes —H for Y≠O and where, in the case of the formula (2), all R cannot simultaneously be H, straight-chain or branched alkyl having 1-20 C atoms, straight-chain or branched alkenyl having 2-20 C atoms and one or more double bonds, straight-chain or branched alkynyl having 2-20 C atoms and one or more triple bonds or saturated, partially or fully unsaturated cycloalkyl having 3-7 C atoms, in particular phenyl, which may be substituted by alkyl groups having 1-6 C atoms, where the substituents R are in each case identical or different, where the substituents R may be bonded to one another in pairs by a single or double bond, where one or more, but not all, the substituents R may be partially or fully substituted by halogens, in particular —F and/or —Cl, or partially by —CN or —NO$_2$, and where one or two non-adjacent carbon atoms of the substituent R may be replaced by atoms and/or atom groups selected from the group —O—, —C(O)—, —C(O)O—, —C(O)NH—, —C(O)NR'—, —S—, —S(O)—, —S(O)NH—, —S(O)NR'—, —S(O)O—, —S(O)$_2$—, —S(O)$_2$O—, —S(O)$_2$NH—, —S(O)$_2$NR'—, —N=, —N=N—, —NH—, —NR'—, —PH—, —PR'—, —P(O)R'—, —P(O)R'—O—, —O—P(O)R'—O— and —PR'$_2$=N— where R'= non-, partially or perfluorinated C$_1$- to C$_6$-alkyl, C$_3$- to C$_7$-cycloalkyl, unsubstituted or substituted phenyl or an unsubstituted or substituted heterocycle.

Besides hydrogen, suitable substituents R of the organic bases used in accordance with the invention are thus: C$_1$- to C$_{20}$-, in particular C$_1$- to C$_{12}$-alkyl groups, and saturated or unsaturated, i.e. also aromatic, C$_3$- to C$_7$-cycloalkyl groups, which may be substituted by C$_1$- to C$_6$-alkyl groups, in particular phenyl. In the case of a base of the formula (2), however, all R cannot simultaneously be hydrogen, i.e. the base cannot be H$_2$O, H$_2$S or H$_2$Se.

An alkyl group having 1 to 12 C atoms is taken to mean, for example, methyl, ethyl, isopropyl, propyl, butyl, sec-butyl, or tert-butyl, furthermore also pentyl, 1-, 2- or 3-methylbutyl, 1,1-, 1,2- or 2,2-dimethylpropyl, 1-ethylpropyl, hexyl, heptyl, octyl, nonyl, decyl, undecyl or dodecyl. The alkyl groups may also be partially or fully substituted by halogens, in particular —F and/or —Cl. Fluorinated alkyl groups are difluoromethyl, trifluoromethyl, pentafluoroethyl, pentafluoropropyl, heptafluoropropyl, heptafluorobutyl or nonafluorobutyl. Perfluoroalkyl group means that all H atoms of the alkyl group have been replaced by F atoms.

A straight-chain or branched alkenyl having 2 to 20 C atoms, in which a plurality of double bonds may also be present, is, for example, allyl, 2- or 3-butenyl, isobutenyl, sec-butenyl, furthermore 4-pentenyl, isopentenyl, hexenyl, heptenyl, octenyl, —C$_9$H$_{17}$, —C$_{10}$H$_{19}$ to —C$_{20}$H$_{39}$; preferably allyl, 2- or 3-butenyl, isobutenyl, sec-butenyl, preference is furthermore given to 4-pentenyl, isopentenyl or hexenyl.

A straight-chain or branched alkynyl having 2 to 20 C atoms, in which a plurality of triple bonds may also be present, is, for example, ethynyl, 1- or 2-propynyl, 2- or 3-butynyl, furthermore 4-pentynyl, 3-pentynyl, hexynyl, heptynyl, octynyl, —C$_9$H$_{15}$, —C$_{10}$H$_{17}$ to —C$_{20}$H$_{37}$, preferably ethynyl, 1- or 2-propynyl, 2- or 3-butynyl, 4pentynyl, 3-pentynyl or hexynyl.

Unsubstituted saturated or partially or fully unsaturated cycloalkyl groups having 3-7 C atoms are therefore cyclopropyl, cyclobutyl, cyclopentyl, cyclohexyl, cycloheptyl, cyclopentenyl, cyclopenta-1,3-dienyl, cyclohexenyl, cyclohexa-1,3-dienyl, cyclohexa-1,4-dienyl, phenyl, cycloheptenyl, cyclohepta-1,3-dienyl, cyclohepta-1,4-dienyl or cyclohepta-1,5-dienyl, which may be substituted by C$_1$- to C$_6$-alkyl groups, where the cycloalkyl group or the cycloalkyl group substituted by C$_1$- to C$_6$-alkyl groups may in turn also be substituted by halogen atoms, such as F, Cl, Br or I, in particular F or Cl, CN or NO$_2$.

The three or two substituents R of the organic base may be identical or different. The substituents R may also be bonded in pairs in such a way that mono-, bi- or polycyclic bases are formed, for example preferably the heterocycles compounds pyridine, imidazole, pyrazole, triazole, pyridazine, pyrimidine, pyrazine, thiazole, oxazole, benzoxazole, benzothiazole, pyrrolidine, piperidine, piperazine, morpholine, indole, indoline, quinoline, isoquinoline or aniline, each of which may optionally be substituted by straight-chain or branched alkyl having 1-20 C atoms, straight-chain or branched alkenyl having 2-20 C atoms and one or more double bonds, straight-chain or branched alkynyl having 2-20 C atoms and one or more triple bonds or saturated, partially or fully unsaturated cycloalkyl having 3-7 C atoms, in particular phenyl, which may be substituted by alkyl groups having 1-6 C atoms.

The heterocycles indicated are preferably unsubstituted or substituted by straight-chain or branched alkyl groups having 1-20 C atoms, in particular 1-12 C atoms.

The substituents R may be partially or fully substituted by halogen atoms, in particular by F and/or Cl, or partially by CN or NO$_2$, but where all substituents R must not be in fully halogenated form. Furthermore, the substituents R may contain one or two non-adjacent heteroatoms or atom groups selected from the group O, C(O), C(O)O, C(O)NH, C(O)NR', S, S(O), S(O)NH, S(O)NR', S(O)O, SO$_2$, SO$_2$O, SO$_2$NH, SO$_2$NR', N, N=N, NH, NR', PH, PR', P(O)R', P(O)R'O, OP(O)R'O and PR'$_2$=N, where R' can be a non-, partially or perfluorinated C$_1$- to C$_6$-alkyl, C$_3$- to C$_7$-cycloalkyl, unsubstituted or substituted phenyl or an unsubstituted or substituted heterocycle.

In R', C$_3$- to C$_7$-cycloalkyl is, for example, cyclopropyl, cyclobutyl, cyclopentyl, cyclohexyl or cycloheptyl.

In R', substituted phenyl denotes phenyl which is substituted by C$_1$- to C$_6$-alkyl, C$_1$- to C$_6$-alkenyl, NO$_2$, F, Cl, Br, I, OH, C$_1$-C$_6$-alkoxy, CN, SCN, SCF$_3$, SO$_2$CF$_3$, C(O)O—C$_1$-C$_6$-alkyl, NH$_2$, C$_1$-C$_6$-alkylamino or C$_1$-C$_6$-dialkylamino, C(O)NR"$_2$, SO$_2$OR", SO$_2$X', SO$_2$NR"$_2$ or NHC(O)R", where X' denotes F, Cl or Br and R" denotes a non-, partially or perfluorinated C$_1$- to C$_6$-alkyl or C$_3$- to C$_7$-cycloalkyl as defined for R', for example o-, m- or p-methylphenyl, o-, m- or p-ethylphenyl, o-, m- or p-propylphenyl, o-, m- or p-isopropylphenyl, o-, m- or p-tert-butylphenyl, o-, m- or p-aminophenyl, o-, m- or p-(N,N-dimethylamino)phenyl, o-, m- or p-nitrophenyl, o-, m- or p-hydroxyphenyl, o-, m- or p-methoxyphenyl, o-, m- or p-ethoxyphenyl, o-, m-, p-(trifluoromethyl)phenyl, o-, m-, p-(trifluoromethoxy)phenyl, o-, m-, p-(trifluoromethylsulfonyl)phenyl, o-, m- or p-fluorophenyl, o-, m- or p-chlorophenyl, o-, m- or p-bromophenyl, o-, m- or p-iodophenyl, furthermore preferably 2,3-, 2,4-, 2,5-, 2,6-, 3,4- or 3,5-dimethylphenyl, 2,3-, 2,4-, 2,5-, 2,6-, 3,4- or 3,5-dihydroxyphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3-, 2,4-, 2,5-, 2,6-, 3,4- or 3,5-dimethoxyphenyl, 5-fluoro-2-methylphenyl, 3,4,5-trimethoxyphenyl or 2,4,5-trimethylphenyl.

In R', heterocycle is taken to mean a saturated or unsaturated mono- or bicyclic heterocyclic radical having 5 to 13 ring members, where 1, 2 or 3 N and/or 1 or 2 S or O atoms may be present and the heterocyclic radical may be mono- or polysubstituted by $C_1$- to $C_6$-alkyl, $C_1$- to $C_6$-alkenyl, $NO_2$, F, Cl, Br, I, OH, $C_1$-$C_6$-alkoxy, CN, SCN, $SCF_3$, $SO_2CF_3$, C(O)O—$C_1$-$C_6$-alkyl, $NH_2$, $C_1$-$C_6$-alkylamino or $C_1$-$C_6$-dialkylamino, C(O)NR"$_2$, $SO_2$OR", $SO_2$X', $SO_2$NR"$_2$ or NHC(O)R", where X' and R" have a meaning indicated above.

The heterocyclic radical is preferably substituted or unsubstituted 2- or 3-furyl, 2- or 3-thienyl, 1-, 2- or 3-pyrrolyl, 1-, 2-, 4- or 5-imidazolyl, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -4- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2, 4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-1H-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 2-, 3-, 4-, 5-, 6-, 7- or 8-quinolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl, 2-, 4-, 5-, 6-, 7- or 8-quinazolinyl or 1-, 2- or 3-pyrrolidinyl.

Without restricting generality, examples of substituents R of the organic bases used in accordance with the invention are:

—$CH_3$, —$C_2H_5$, —$C_3H_7$, —$CH(CH_3)_2$, —$C_4H_9$, —$C(CH_3)_3$, —$C_5H_{11}$, —$C_6H_{13}$, —$C_7H_{15}$, —$C_8H_{17}$, —$C_9H_{19}$, —$C_{10}H_{21}$, —$C_{12}H_{25}$, —$C_{20}H_{41}$, —$OCH_3$, —OCH$(CH_3)_2$, —$CH_2OCH_3$, —$C_2H_4OCH(CH_3)_2$, —$SCH_3$, —$SCH(CH_3)_2$, —$C_2H_4SC_2H_5$, —$C_2H_4SCH(CH_3)_2$, —S(O)$CH_3$, —$CH_2SO_2CH_3$, —$OSO_2CH_3$, —$CH_2N(H)C_2H_5$, —$C_2H_4N(H)C_2H_5$, —$CH_2N(CH_3)CH_3$, —$C_2H_4N(CH_3)$ $CH_3$, —$N(CH_3)_2$, —$N(CH_3)C_3H_5$, —$N(CH_3)CF_3$, —O—$C_4H_8$—O—$C_4H_9$, —S—$C_2H_4$—$N(C_4H_9)_2$, —$CF_3$, —$C_2F_5$, —$C_3F_7$, —$C_4F_9$, —$C(CF_3)_3$, —$CF_2SO_2CF_3$, —$C_2F_4N(C_2F_5)C_2F_5$, —$CFH_2$, —$CHF_2$, —$CH_2CF_3$, —$C_2F_2H_3$, —$C_3FH_6$, —$CH_2C_3F_7$, —$C(CFH_2)_3$, —CHO, —$CH_2C(O)CH_3$, —$CH_2C(O)C_2H_5$, —$CH_2C(O)OCH_3$, $CH_2C(O)OC_2H_5$, —C(O)$CH_3$, —C(O)$OCH_3$, —CH=$CH_2$, —$CH_2$CH=$CH_2$, —C($CH_3$)=$CH_2$, —CH=CH$CH_3$, —$CH_2$CH=CH$CH_3$, —O—CH=$CH_2$, —O—$CH_2$CH=$CH_2$, —C≡CH, —$CH_2$C≡CH, —C≡C$CH_3$, —$CH_2$C≡C$CH_3$,

  

-continued

  
 
 
  
  
 
 

The choice of a suitable base for the process according to the invention presents the person skilled in the art with absolutely no difficulties. Particular preference is given in accordance with the invention to bases selected from the group $(C_2H_5)_3N$, $(C_2H_5)_2NH$, $(C_2H_5)_3P$, $(C_2H_5O)_3P$, $(C_4H_9)_3P$, $CH_3$—S—$CH_3$, $(CH_3)_2N$—C(O)—$N(CH_3)_2$, $C_6H_5$—Se—$C_6H_5$, guanidine, pyridine, imidazole, N-methylimidazole, benzoxazole, benzothiazole, pyrrolidine, piperidine, piperazine, aniline, N,N-dimethylaniline, benzylamine, N-ethylbenzylamine or diphenyl sulfide.

The suitable alcohol is selected so that the desired cation is formed after alkylation of the base used. The corresponding choice presents the person skilled in the art with absolutely no difficulties. Without restricting generality, the alcohol, to be described in terms of a formula by $R^{OH}$—OH, used for the process according to the invention is preferably an aliphatic alcohol, i.e. $R^{OH}$ in this case denotes an aliphatic group. Particular preference is given to process variants in which an alcohol selected from the group methanol, ethanol, isopropanol, n-propanol, allyl alcohol, butanol, hexanol or benzyl alcohol, but also fluorinated aliphatic alcohols, such as 4,5,5-trifluoropent-4-en-1-ol or 3,3,4,4,5,5,5-heptafluoropentan-1-ol, is employed.

The tris(perfluoroalkyl)phosphine oxides used in accordance with the invention can be prepared by conventional methods known to the person skilled in the art. These compounds are preferably prepared by reaction with hexamethyldisiloxane (V. Ya. Sememii et al., J. Gen. Chem. USSR (Engl. Trans.) 55, No. 12 (1985), 2415-2417). The corresponding descriptions are incorporated herein by way of reference and are regarded as part of the disclosure.

Use can also be made in accordance with the invention of mixtures of two or more tris(perfluoroalkyl)phosphine oxides. Preferably, only one tris(perfluoroalkyl)phosphine oxide is reacted in each case in the process according to the invention.

The tris(perfluoroalkyl)phosphine oxides used in accordance with the invention or corresponding derivatives thereof have three perfluoroalkyl groups, abbreviated to $R^F$ above, which are identical or different. Preference is given to the use of tris(perfluoroalkyl)phosphine oxides having identical perfluoroalkyl groups in each case.

In a preferred embodiment of the process according to the invention, use is made of a tris(perfluoroalkyl)phosphine oxide in which the perfluoroalkyl groups contain 1 to 20 C atoms and are straight-chain or branched. Particular preference is given to starting materials whose perfluoroalkyl groups have 1 to 12 C atoms.

Without restricting generality, the tris(perfluoroalkyl) phosphine oxide used is a compound selected from the group $(CF_3)_3P(O)$, $(C_2F_5)_3P(O)$, $(C_3F_7)_3P(O)$ and $(C_4F_9)_3P(O)$.

A suitable reaction medium for the process according to the invention is preferably a conventional polar or nonpolar solvent known to the person skilled in the art. Alternatively, the process according to the invention can also be carried out without solvent. Without restricting generality, the polar solvent used is particularly preferably dichloromethane, 1,2-dimethoxyethane, benzene or a mixture thereof.

The temperature at which the reaction is preferably carried out in accordance with the invention is between −20° C. and 200° C. The reaction is particularly preferably carried out at a temperature of 0° C. to 100° C. The reaction temperature is very particularly preferably room temperature.

In a preferred variant of the process according to the invention, [lacuna] is carried out without an excess or with an up to five-fold excess of one of the reactants, based on the molar amount. The reaction is particularly preferably carried out using approximately equimolar amounts of the starting materials.

The present invention furthermore relates to the organic salts containing bis(perfluoroalkyl)phosphinate anions prepared by the process according to the invention.

The compounds prepared by the process according to the invention have a salt-like character, relatively low melting points (usually below 100° C.) and can be used as ionic liquids.

The salts prepared by the process according to the invention can be employed as solvents for many synthetic or catalytic reactions, for example Friedel-Crafts acylation and alkylation, Diels-Alder cycloadditions, hydrogenation and oxidation reactions, Heck reactions, Suzuki couplings, hydroformylations.

It is also possible to use the compounds prepared by the process according to the invention as non-aqueous electrolyte, optionally in combination with other electrolytes known to the person skilled in the art, or as conductive salt in electrochemical cells.

In addition, the salts prepared by the process according to the invention can be used as non-aqueous polar substances in suitable reactions as phase-transfer catalyst, as surfactant (surface active agent), as plasticiser or as medium for the heterogenisation of homogeneous catalysts.

A general scheme summarises the process according to the invention:

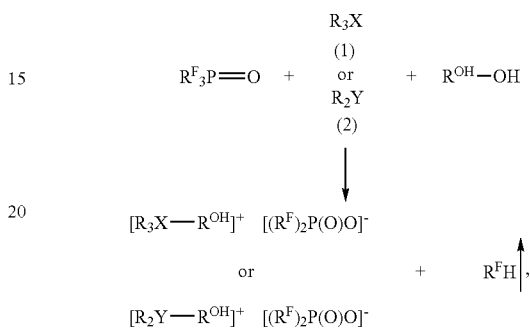

where $R^F$, R, X, Y and $R^{OH}$ have a meaning indicated in the description. The arrow indicated in the case of the monohydroperfluoroalkane $R^FH$ means that the compound is volatile.

The complete disclosure content of all applications, patents and publications mentioned above and below is incorporated into this application by way of reference.

Even without further comments, it is assumed that a person skilled in the art will be able to utilise the above description in the broadest scope. The preferred embodiments and examples should therefore merely be regarded as descriptive disclosure which is absolutely not limiting in any way.

The NMR spectra were measured on solutions in deuterated solvents at 20° C. on a Bruker Avance 300 spectrometer with a 5 mm $^1$H/BB broad-band head with deuterium lock. The measurement frequencies of the various nuclei are: $^1$H: 300.13 MHz, $^{11}$B: 96.92 MHz, $^{19}$F: 282.41 MHz and $^{31}$P: 121.49 MHz. The referencing method is indicated separately for each spectrum or each data set.

EXAMPLES

Example 1

N-Ethylpyridinium bis(pentafluoroethyl)phosphinate

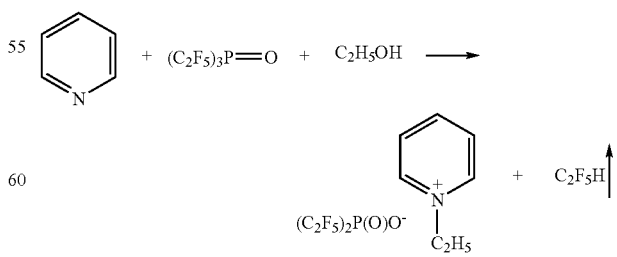

15.69 g (38.8 mmol) of tris(pentafluoroethyl)phosphine oxide, $(C_2F_5)_3P$=O, are mixed with 20 cm³ of dichloromethane and 3.09 g (39.1 mmol) of pyridine in a 50 ml flask fitted with a reflux condenser cooled to −65 to −70° C. 1.85 g (40.2 mmol) of ethanol are added over the course of 15 minutes at room temperature while the reaction mixture is stirred using a magnetic stirrer. The reflux condenser is warmed to room temperature, and the dichloromethane is distilled off. The residue is dried at 60° C. under a vacuum of 1.4 Pa, giving 14.56 g of a dark-red, very viscous material. The yield of N-ethylpyridinium bis(pentafluoroethyl)phosphinate is 91.7%.

$^{19}$F NMR (reference: CCl$_3$F—internal standard; solvent: CD$_3$CN): −80.13 m (2CF$_3$); −124.81 dm (2CF$_2$); $^2J_{P,F}$=67 Hz.

$^1$H NMR (reference: TMS; solvent: CD$_3$CN): 1.59 t (CH$_3$); 4.59 q (CH$_2$); 8.03 m (2CH); 8.50 tt (CH); 8.78 m (2CH); $^3J_{H,H}$=7.3 Hz; $^3J_{H,H}$=7.8 Hz; $^4J_{H,H}$=1.2 Hz.

$^{31}$P NMR (reference: 85% H$_3$PO$_4$; solvent: CD$_3$CN): −2.19 quin.; $^2J_{P,F}$=67 Hz.

Example 2

Ethyidimethylsulfonium bis(pentafluoroethyl)phosphinate

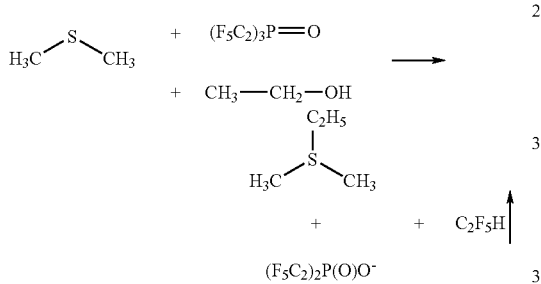

4.92 g (12.2 mmol) of tris(pentafluoroethyl)phosphine oxide, (C$_2$F$_5$)$_3$P═O, are mixed with 20 cm$^3$ of 1,2-dimethoxyethane and 0.775 g (12.5 mmol) of dimethyl sulfide in a 50 ml flask fitted with a reflux condenser. 0.560 g (12.2 mmol) of ethanol are added over the course of 1 minute at room temperature while the reaction mixture is stirred using a magnetic stirrer. The reaction mixture is boiled under reflux for 5 hours, and the 1,2-dimethoxyethane is distilled off. The residue is dried at 40° C. under a vacuum of 1.4 Pa, giving 4.18 g of a solid material. The yield of ethyidimethylsulfonium bis(pentafluoroethyl)phosphinate is 87.4%.

$^{19}$F NMR (reference: CCl$_3$F—internal standard; solvent: CD$_3$CN): −80.19 m (2CF$_3$); −124.96 dm (2CF$_2$); $^2J_{P,F}$=69 Hz.

$^1$H NMR (reference: TMS; solvent: CD$_3$CN): 1.37 t (CH$_3$); 2.81 s (2CH$_3$); 3.28 q (CH$_2$); $^3J_{H,H}$=7.4 Hz.

$^{31}$P NMR (reference: 85% H$_3$PO$_4$; solvent: CD$_3$CN): −1.86 quin.; $^2J_{P,F}$=69 Hz.

Example 3

N-Methylbenzoxazolium bis(pentafluoroethyl)phosphinate

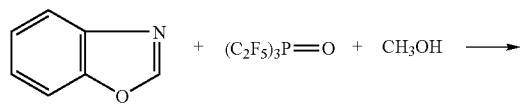

-continued

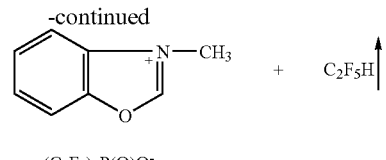

9.40 g (23.3 mmol) of tris(pentafluoroethyl)phosphine oxide, (C$_2$F$_5$)$_3$P═O, are mixed with 20 cm$^3$ of dry 1,2-dimethoxyethane and 2.77 g (23.3 mmol) of benzoxazole in a 50 ml flask fitted with a reflux condenser. 0.745 g (23.3 mmol) of methanol are added over the course of 5 minutes at room temperature while the reaction mixture is stirred using a magnetic stirrer. The reaction mixture is stirred for 1 hour, and the 1,2-dimethoxyethane is distilled off. The residue is dried at 40° C. under a vacuum of 1.4 Pa, giving 9.44 g of a solid material (melting point 78-79° C.). The yield of N-methylbenzoxazolium bis(pentafluoroethyl)phosphinate is 93.1%.

$^{19}$F NMR (reference: CCl$_3$F—internal standard; solvent: CD$_3$CN): −80.16 m (2CF$_3$); −124.93 dm (2CF$_2$); $^2J_{P,F}$=71 Hz.

$^1$H NMR (reference: TMS; solvent: CD$_3$CN): 4.20 d (CH$_3$); 7.85 m (2CH); 8.01 m (2CH); 10.05 br. s (CH); $^4J_{H,H}$=1.0 Hz.

$^{31}$P NMR (reference: 85% H$_3$PO$_4$; solvent: CD$_3$CN): −1.77 quin.; $^2J_{P,F}$=71 Hz.

Example 4

Triethyl-i-propylammonium bis(pentafluoroethyl)phosphinate

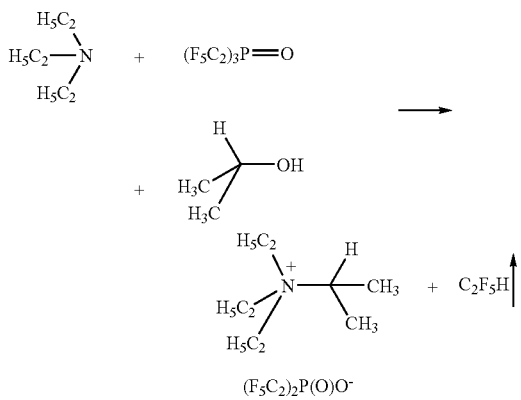

9.30 g (23.0 mmol) of tris(pentafluoroethyl)phosphine oxide, (C$_2$F$_5$)$_3$P═O, are mixed with 8.34 g (82.4 mmol) of triethylamine in a 50 ml flask fitted with a reflux condenser and a magnetic stirrer. 1.41 g (23.5 mmol) of i-propanol are added to this reaction mixture at 0° C. (ice-bath cooling) with stirring. The reaction mixture is stirred at 0° C. for 5 hours and at room temperature for 36 hours. All volatile products are removed at 50° C. under a high vacuum of 1.4 Pa, giving 9.25 g of a solid material consisting of 37% of triethylammonium bis(pentafluoroethyl)phosphinate and 63% of triethyl-i-propylammonium bis(pentafluoro-ethyl)phosphinate.

In order to isolate the triethyl-i-propylammonium bis(pentafluoroethyl)phosphinate, this mixture is dissolved in 15 cm³ of water and treated with aqueous KOH (0.477 g of KOH in 5 cm³ of water) at room temperature. The water is removed in a rotary evaporator, and the residue is dried for three hours at 50° C. under a high vacuum (1.4 Pa), giving 8.70 g of a solid material, which are suspended in 15 cm³ of dichloromethane, the sediment is filtered off and washed twice on the filter with 5 cm³ of dichloromethane. After removal of the dichloromethane, 5.9 g of a solid salt are obtained. The yield of triethyl-i-propylammonium bis(pentafluoroethyl)phosphinate is 57.7%, based on tris(pentafluoroethyl)phosphine oxide.

$^{19}$F NMR (reference: CCl$_3$F—internal standard; solvent: CD$_3$CN): −80.18 m (2CF$_3$); −124.89 dm (2CF$_2$); $^2J_{P,F}$=66 Hz.

$^1$H NMR (reference: TMS; solvent: CD$_3$CN): 1.29 tm (3CH$_3$); 1.38 dm (2CH$_3$); 3.31 q (3CH$_2$); 3.71 hep. (CH); $^3J_{H,H}$=7.3 Hz; $^3J_{H,H}$=6.7 Hz.

$^{31}$P NMR (reference: 85% H$_3$PO$_4$; solvent: CD$_3$CN): −2.32 quin. (1P); $^2J_{P,F}$=66 Hz.

Example 5

Ethyltributylphosphonium bis(pentafluoroethyl)phosphinate

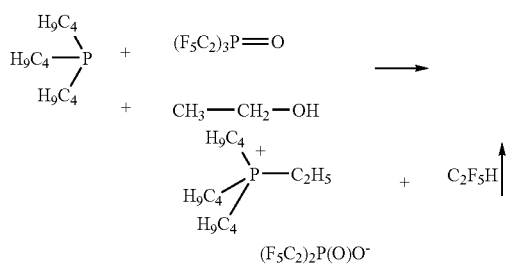

12.00 g (29.7 mmol) of tris(pentafluoroethyl)phosphine oxide, (C$_2$F$_5$)$_3$P=O, are mixed with 20 cm³ of dichloromethane and 6.00 g (29.7 mmol) of tributylphosphine in a 50 ml flask fitted with a reflux condenser held at minus 65 to minus 70° C. 1.37 g (29.7 mmol) of ethanol are added over the course of 3 minutes at room temperature while the reaction mixture is stirred using a magnetic stirrer. The reflux condenser is warmed to room temperature, and the dichloromethane is distilled off. The residue is dried at 60° C. under a vacuum of 1.4 Pa, giving 15.60 g of a solid material (melting point 42-43° C.). The yield of ethyltributylphosphonium bis(pentafluoroethyl)phosphinate is 98.7%.

$^{19}$F NMR (reference: CCl$_3$F—internal standard; solvent: CD$_3$CN): −80.21 m (2CF$_3$); −124.89 dm (2CF$_2$); $^2J_{P,F}$=65 Hz.

$^1$H NMR (reference: TMS; solvent: CD$_3$CN): 0.94 t (3CH$_3$); 1.17 dt (CH$_3$); 1.46 m (6CH$_2$); 2.11 m (3CH$_2$); 2.15 dq (CH$_2$); $^3J_{H,H}$=7.1 Hz; $^3J_{H,H}$=7.6 Hz; $^3J_{P,H}$=13.0 Hz; $^4J_{P,H}$=18.2 Hz.

$^{31}$P NMR (reference: 85% H$_3$PO$_4$; solvent: CD$_3$CN): 34.73 br. s (1P); −2.39 quin. (1P); $^2J_{P,F}$=65 Hz.

Example 6

Tetraethylammonium bis(pentafluoroethyl)phosphinate

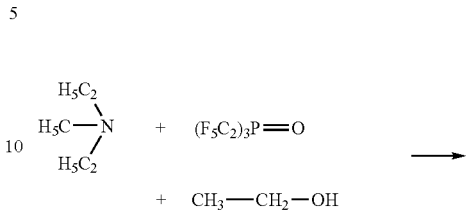

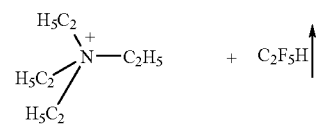

12.62 g (31.2 mmol) of tris(pentafluoroethyl)phosphine oxide, (C$_2$F$_5$)$_3$P=O, are mixed with 20 cm³ of dichloromethane and 3.16 g (31.2 mmol) of triethylamine in a 50 ml flask fitted with a reflux condenser held at minus 65 to minus 70° C. 1.44 g (31.2 mmol) of ethanol are added over the course of 3 minutes at room temperature while the reaction mixture is stirred using a magnetic stirrer. The reflux condenser is warmed to room temperature, and the dichloromethane is distilled off. The residue is dried at 60° C. under a vacuum of 1.4 Pa, giving 13.07 g of a solid material (melting point 103-105° C.). The yield of tetraethylammonium bis (pentafluoroethyl)phosphinate is 97.1%.

$^{19}$F NMR (reference: CCl$_3$F—internal standard; solvent: CD$_3$CN): −80.23 m (2CF$_3$); −124.94 dm (2CF$_2$); $^2J_{P,F}$=65 Hz.

$^1$H NMR (reference: TMS; solvent: CD$_3$CN): 1.20 tm (CH$_3$); 3.18 q (CH$_2$); $^3J_{H,H}$=7.3 Hz.

$^{31}$P NMR (reference: 85% H$_3$PO$_4$; solvent: CD$_3$CN): −2.33 quin.; $^2J_{P,F}$=65 Hz.

Example 7

N-Ethylbenzothiazolium bis(pentafluoroethyl)phosphinate

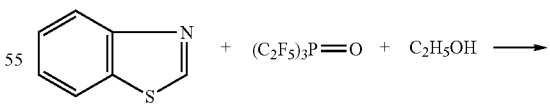

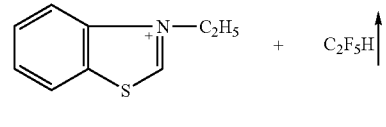

10.74 g (26.6 mmol) of tris(pentafluoroethyl)phosphine oxide, (C$_2$F$_5$)$_3$P=O, are mixed with 20 cm³ of dichloromethane and 3.53 g (26.1 mmol) of benzothiazole in a 50 ml flask fitted with a reflux condenser held at minus 65 to minus 70° C. 1.22 g (26.5 mmol) of ethanol are added over the course of 5 minutes at room temperature while the reaction mixture is stirred using a magnetic stirrer. The reflux condenser is warmed to room temperature, and the dichloromethane is distilled off. The residue is dried at 60° C. under a vacuum of 1.4 Pa, giving 13.07 g of a solid material (melting point 76-77° C.). The yield of N-ethylbenzothiazolium bis(pentafluoroethyl)phosphinate is 82.0%, based on benzothiazole.

$^{19}$F NMR (reference: CCl$_3$F—internal standard; solvent: CD$_3$CN): −80.08 m (2CF$_3$); −124.81 dm (2CF$_2$); $^2J_{P,F}$=67 Hz.

$^1$H NMR (reference: TMS; solvent: CD$_3$CN): 1.66 t (CH$_3$); 4.81 q (CH$_2$); 7.88 m (2CH); 8.30 m (2CH); 10.34 s. (CH); $^3J_{H,H}$=7.3 Hz.

$^{31}$P NMR (reference: 85% H$_3$PO$_4$; solvent: CD$_3$CN): −2.00 quin.; $^2J_{P,F}$=67 Hz.

Example 8

N-N-Dimethylimidazolium bis(pentafluoroethyl)phosphinate

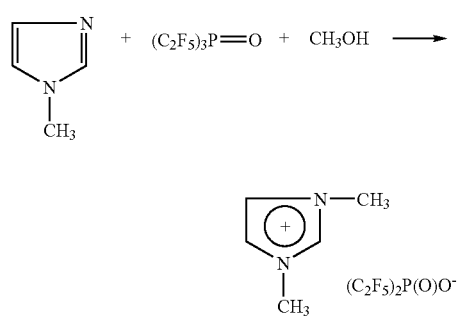

20.49 g (50.7 mmol) of tris(pentafluoroethyl)phosphine oxide, (C$_2$F$_5$)$_3$P═O, are mixed with 30 cm$^3$ of dichloromethane and 4.16 g (50.7 mmol) of N-methylimidazole in a 100 ml flask fitted with a reflux condenser held at minus 65 to minus 70° C. 1.623 g (50.7 mmol) of methanol are added over the course of 15 minutes at room temperature while the reaction mixture is stirred using a magnetic stirrer. The reflux condenser is warmed to room temperature, and the dichloromethane is distilled off. The residue is dried at 60° C. under a vacuum of 1.4 Pa, giving 19.23 g of a solid material. The yield of N,N-dimethylimidazolium bis(pentafluoroethyl)phosphinate is 95.2% (melting point 35-37° C.).

$^{19}$F NMR (reference: CCl$_3$F—internal standard; solvent: CD$_3$CN): −80.18 m (2CF$_3$); −124.90 dm (2CF$_2$); $^2J_{P,F}$=66 Hz.

$^1$H NMR (reference: TMS; solvent: CD$_3$CN): 3.84 d (2CH$_3$); 7.37 d (2CH); 8.61 br. s. (CH); $^4J_{H,H}$=1.6 Hz; $^4J_{H,H}$=0.6 Hz.

$^{31}$P NMR (reference: 85% H$_3$PO$_4$; solvent: CD$_3$CN): −2.16 quin.; $^2J_{P,F}$=66 Hz.

Example 9

N-Methyl-N-ethylimidazolium bis(pentafluoroethyl)phosphinate

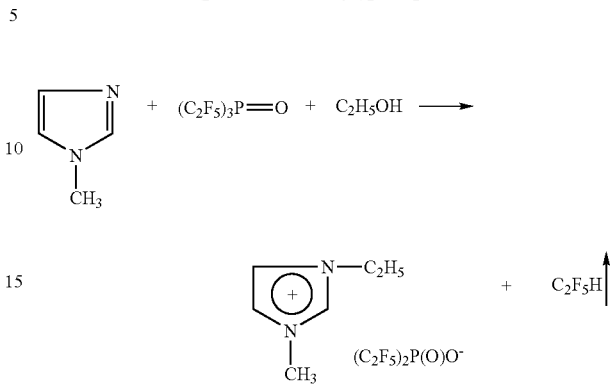

23.22 g (57.5 mmol) of tris(pentafluoroethyl)phosphine oxide, (C$_2$F$_5$)$_3$P═O, are mixed with 30 cm$^3$ of dichloromethane and 4.72 g (57.5 mmol) of N-methylimidazole in a 100 ml flask fitted with a reflux condenser held at minus 65 to minus 70° C. 2.643 g (57.4 mmol) of ethanol are added over the course of 15 minutes at room temperature while the reaction mixture is stirred using a magnetic stirrer. The reflux condenser is warmed to room temperature, and the dichloromethane is distilled off. The residue is dried at 60° C. under a vacuum of 1.4 Pa, giving 21.97 g of a liquid material. The yield of N-methyl-N-ethylimidazolium bis(pentafluoroethyl)phosphinate is 92.9%.

$^{19}$F NMR (reference: CCl$_3$F—internal standard; solvent: CD$_3$CN): −80.17 m (2CF$_3$); −124.90 dm (2CF$_2$); $^2J_{P,F}$=66 Hz.

$^1$H NMR (reference: TMS; solvent: CD$_3$CN): 1.47 t (CH$_3$); 3.87 s (CH$_3$); 4.21 q (CH$_2$); 7.48 dd (CH); 7.56 dd (CH); 9.01 br. s. (CH); $^3J_{H,H}$=7.3 Hz; $J_{H,H}$=1.8 Hz.

$^{31}$P NMR (reference: 85% H$_3$PO$_4$; solvent: CD$_3$CN): −2.07 quin.; $^2J_{P,F}$=67 Hz.

Example 10

2-Methyl-1,1,3,3-tetramethylisouronium bis(pentafluoroethyl)phosphinate

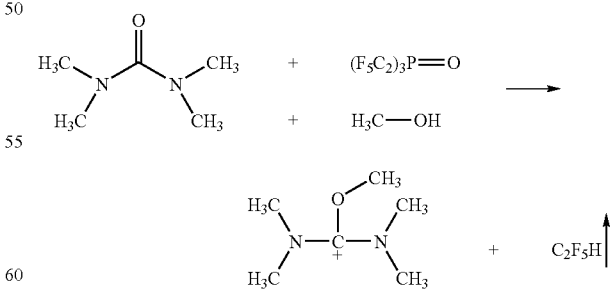

6.72 g (16.6 mmol) of tris(pentafluoroethyl)phosphine oxide, (C$_2$F$_5$)$_3$P═O, are mixed with 15 cm$^3$ of dimethoxyethane and 1.93 g (16.6 mmol) of tetramethylurea in a 25 ml flask fitted with a reflux condenser. 0.532 g (16.6 mmol) of methanol are added to this mixture while the reaction mixture is stirred using a magnetic stirrer. The reaction mixture is boiled for 5 hours, and all volatile products are removed at 50° C. under a high vacuum (1.4 Pa), giving 6.59 g of a viscous liquid. The yield of 2-methyl-1,1,3,3-tetramethylisouronium bis(pentafluoroethyl)phosphinate is 91.9%.

$^{19}$F NMR (reference: CCl$_3$F—internal standard; solvent: CD$_3$CN): −80.21 m (2CF$_3$); −124.91 dm (2CF$_2$); $^2J_{P,F}$=67 Hz.

$^1$H NMR (reference: TMS; solvent: CD$_3$CN): 3.05 s (4CH$_3$); 4.05 s (OCH$_3$).

$^{31}$P NMR (reference: 85% H$_3$PO$_4$; solvent: CD$_3$CN): −2.12 quin.; $^2J_{P,F}$=67 Hz.

Example 11

Methyldiphenylselenonium bis(pentafluoroethyl)phosphinate

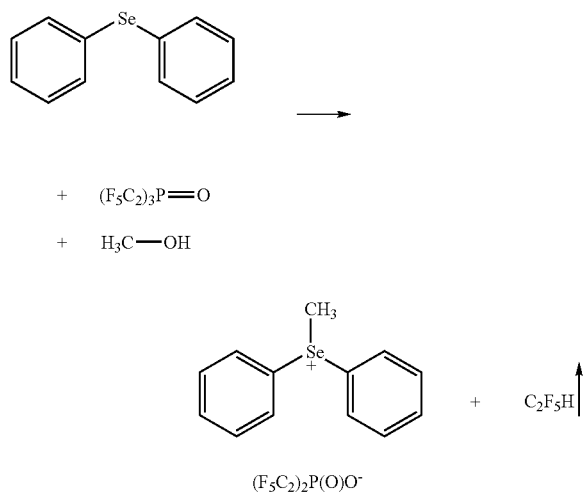

6.08 g (15.05 mmol) of tris(pentafluoroethyl)phosphine oxide, (C$_2$F$_5$)$_3$P=O, are mixed with 15 cm$^3$ of dimethoxyethane and 3.51 g (15.05 mmol) of diphenyl selenide in a 25 ml flask fitted with a reflux condenser. 0.482 g (15.05 mmol) of methanol are added to this mixture while the reaction mixture is stirred using a magnetic stirrer. The reaction mixture is boiled for 8 hours, and all volatile products are removed at 50° C. under a high vacuum (1.4 Pa). The residue is washed with pentane (three times with 5 cm$^3$) and dried for one hour at 50° C. under a vacuum of 1.4 Pa, giving 4.06 g of a yellow-green viscous liquid. The yield of methyldiphenylselenonium bis(pentafluoroethyl)phosphinate is 49.2%.

$^{19}$F NMR (reference: CCl$_3$F—internal standard; CD$_3$CN film): −80.16 m (2CF$_3$); −124.84 dm (2CF$_2$); $^2J_{P,F}$=77 Hz.

$^1$H NMR (reference: TMS; solvent: CD$_3$CN film): 3.39 s (CH$_3$); 7.60-7.80 m (2C$_6$H$_5$).

$^{31}$P NMR (reference: 85% H$_3$PO$_4$; solvent: CD$_3$CN film): −1.15 quin.; $^2J_{P,F}$=77 Hz.

Example 12

1-(4,5,5-Trifluoro-4-pentenyl)-3-methylimidazolium bis(pentafluoroethyl)phosphinate

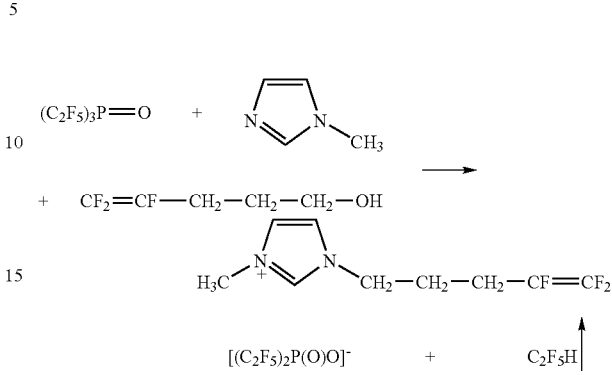

8.61 g (21.3 mmol) of tris(pentafluoroethyl)phosphine oxide, (C$_2$F$_5$)$_3$P=O, are mixed with 20 cm$^3$ of dry benzene and 1.75 g (21.3 mmol) of N-methylimidazole in a flask fitted with a reflux condenser held at minus 25° C. 2.98 g (21.3 mmol) of 4,5,5-trifluoropent-4-en-1-ol are added to this mixture at room temperature while stirring using a magnetic stirrer. The reaction mixture is heated at an oil-bath temperature of 100° C. for 20 minutes. After cooling to room temperature, the phosphinate is separated from the benzene phase and washed twice with 10 cm$^3$ of benzene. Drying at 60° C. (2 hours) under a vacuum of 13.3 Pa gives 10.53 g of 1-(4,5,5-trifluoro-4-pentenyl)-3-methylimidazolium bis(pentafluoroethyl)phosphinate as liquid. The yield is 97.6%.

$^{19}$F NMR (reference: CCl$_3$F—internal standard; CD$_3$CN film): −80.22 m (2CF$_3$); −124.90 dm (2CF$_2$); $^2J_{P,F}$=66 Hz; −105.27 dd (CF); $^2J_{F,F}$=89 Hz; $^3J_{F,F}$=33 Hz; −123.72 dd (CF); $^2J_{F,F}$=89 Hz; $^3J_{F,F}$=113 Hz; −174.2 ddt (CF); $^2J_{F,F}$=89 Hz; $^3J_{F,F}$=113 Hz; $^3J_{F,H}$=21 Hz.

$^1$H NMR (reference: TMS; solvent: CD$_3$CN film): 2.08 quin (CH$_2$); $^3J_{H,H}$=7.4 Hz; 2.36 dddt (CH$_2$); $^3J_{H,H}$=7.4 Hz; $^3J_{F,H}$=21 Hz; $^4J_{H,H}$=4 Hz; $^4J_{H,F}$=3 Hz; 3.82 s (CH$_3$); 4.19 t (CH$_2$); $^3J_{H,H}$=7 Hz; 7.37 dd (CH); $^3J_{H,H}$=7.3 Hz; $J_{H,H}$=1.5 Hz; 7.42 dd (CH); $^3J_{H,H}$=7.3 Hz; $J_{H,H}$=1.5 Hz; 8.66 br.s. (CH).

$^{31}$P NMR (reference: 85% H$_3$PO$_4$; solvent: CD$_3$CN film): −1.61 quinsep; $^2J_{P,F}$=66 Hz; $^3J_{P,F}$=1 Hz.

Example 13

1-(3,3,4,4,5,5,5-Heptafluoropentyl)-3-methylimidazolium bis(pentafluoroethyl)phosphinate

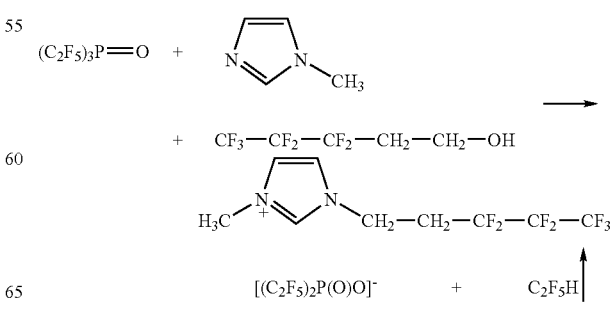

8.27 g (20.5 mmol) of tris(pentafluoroethyl)phosphine oxide, $(C_2F_5)_3P=O$, are mixed with 20 cm$^3$ of dry benzene and 1.67 g (20.3 mmol) of N-methylimidazole in a flask fitted with a reflux condenser held at minus 25° C. 4.37 g (20.4 mmol) of 3,3,4,4,5,5,5-heptafluoropentan-1-ol are added to this mixture at room temperature while stirring using a magnetic stirrer. The reaction mixture is heated at an oil-bath temperature of 100° C. for 20 minutes. After cooling to room temperature, the phosphinate is separated from the benzene phase and washed twice with 10 cm$^3$ of benzene. Drying at 60° C. (2 hours) under a vacuum of 13.3 Pa gives 11.55 g of 1-(3,3,4,4,5,5,5-heptafluoropentyl)-3-methylimidazolium bis(pentafluoroethyl)phosphinate as liquid. The yield is 97.5%.

$^{19}$F NMR (reference: CCl$_3$F—internal standard; CD$_3$CN film): −80.26 m (2CF$_3$); −80.16 t (CF$_3$), $^4J_{F,F}$=9 Hz; −124.92 dm (2CF$_2$); $^2J_{P,F}$=66 Hz; −114.23 qt (CF$_2$); $^3J_{F,H}$=18.5 Hz; $^4J_{F,F}$=9 Hz; −127.33 s (CF$_2$).

$^1$H NMR (reference: TMS; solvent: CD$_3$CN film): 2.82 ttt (CH$_2$); $^3J_{H,F}$=18.5 Hz; $^3J_{H,H}$=7.1 Hz; $^4J_{H,F}$=1.3 Hz; 3.83 s (CH$_3$); 4.51 t (CH$_2$); $^3J_{H,H}$=7.1 Hz; 7.38 dd (CH); $^3J_{H,H}$=7.1 Hz; $^3J_{H,H}$=1.5 Hz; 7.51 dd (CH); $^3J_{H,H}$=7.1 Hz; $^3J_{H,H}$=1.5 Hz; 8.79 br.s. (CH).

$^{31}$P NMR (reference: 85% H$_3$PO$_4$; solvent: CD$_3$CN film): −1.59 quinsep; $^2J_{P,F}$=66 Hz; $^3J_{P,F}$=1 Hz.

Example 14

1-Allyl-3-methylimidazolium bis(pentafluoroethyl)phosphinate

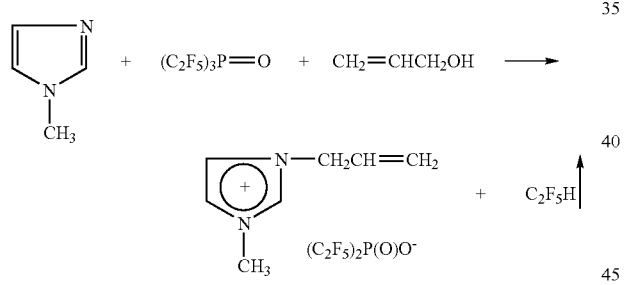

17.81 g (44.1 mmol) of tris(pentafluoroethyl)phosphine oxide, $(C_2F_5)_3P=O$, are mixed with 20 cm$^3$ of dry benzene and 3.62 g (44.1 mmol) of N-methylimidazole in a flask fitted with a reflux condenser held at minus 65°-70° C. 2.56 g (44.1 mmol) of allyl alcohol are added to this mixture over the course of 15 minutes at room temperature while stirring using a magnetic stirrer. The reflux condenser is warmed to room temperature, and the benzene is distilled off. The residue is dried at 80° C. under a vacuum of 13 Pa, giving 16.97 g of a viscous liquid material. The yield of 1-allyl-3-methylimidazolium bis(pentafluoroethyl)phosphinate is 90.7%.

$^{19}$F NMR (reference: CCl$_3$F—internal standard; CD$_3$CN): −80.14 m (2CF$_3$); −124.90 dm (2CF$_2$); $^2J_{P,F}$=66 Hz.

$^1$H NMR (reference: TMS; solvent: CD$_3$CN): 3.83 s (CH$_2$); 4.75 d,m (CH$_2$); $^3J_{H,H}$=6.1 Hz; 5.35 d,m (CH); $^3J_{H,H}$=16.8 Hz; 5.38 d,d (CH); $^3J_{H,H}$=10.3 Hz; J$_{H,H}$=1.0 Hz; 6.00 d,d,t (CH); $^3J_{H,H}$=16.8 Hz; $^3J_{H,H}$=10.3 Hz; $^3J_{H,H}$=6.3 Hz; 7.39 m (CH); 7.40 m (CH); 8.73 br.s. (CH).

$^{31}$P NMR (reference: 85% H$_3$PO$_4$; solvent: CD$_3$CN): −2.48 quin; $^2J_{P,F}$=66 Hz.

The invention claimed is:

1. Process for the preparation of organic salts of bis(perfluoroalkyl)phosphinate anions of the formula $[(R^F)_2P(O)(O)]^-$, wherein $R^F$ in each case, independently of one another, denotes a perfluoroalkyl, comprising at least the reaction of a tris(perfluoroalkyl)phosphine oxide with an alcohol and an organic base which is more strongly basic than the alcohol.

2. Process for the preparation of organic salts of bis(perfluoroalkyl)phosphinate anions according to claim 1, wherein the organic base employed is a compound of the general formula (1)

$$R_3X \quad (1)$$

or of the general formula (2)

$$R_2Y \quad (2)$$

in which

X denotes

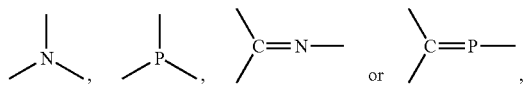

Y denotes —O—, —S—, —Se—, —C(=O)—, —C(=S)— or —C(=Se)—,

R denotes H for Y≠O and where, in the case of the formula (2), all R cannot simultaneously be H, straight-chain or branched alkyl having 1-20 C atoms, straight-chain or branched alkenyl having 2-20 C atoms and one or more double bonds, straight-chain or branched alkynyl having 2-20 C atoms and one or more triple bonds or saturated, partially or fully unsaturated cycloalkyl having 3-7 C atoms, in particular phenyl, which may be substituted by alkyl groups having 1-6 C atoms, where the substituents R are in each case identical or different, where the substituents R may be bonded to one another in pairs by a single or double bond, where one or more, but not all, the substituents R may be partially or fully substituted by halogens, in particular —F and/or —Cl, or partially by —CN or —NO$_2$, and where one or two non-adjacent carbon atoms of the substituent R may be replaced by atoms and/or atom groups selected from the group —O—, —C(O)—, —C(O)O—, —C(O)NH—, —C(O)NR'—, —S—, —S(O)—, —S(O)NH—, —S(O)NR'—, —S(O)O—, —S(O)$_2$—, —S(O)$_2$O—, —S(O)$_2$NH—, —S(O)$_2$NR'—, —N=, —N=N—, —NH—, —NR'—, —PH—, —PR'—, —P(O)R'—, —P(O)R'—O—, —O—P(O)R'—O— and —PR'$_2$=N— where R'=non-fluorinated, partially fluorinated or perfluorinated C$_1$- to C$_6$-alkyl, C$_3$- to C$_7$-cycloalkyl, unsubstituted or substituted phenyl or an unsubstituted or substituted heterocycle.

3. Process according to claim 1, wherein the organic base employed is $(C_2H_5)_3N$, $(C_2H_5)_2NH$, $(C_2H_5)_3P$, $(C_2H_5O)_3P$, $(C_4H_9)_3P$, $CH_3$—S—$CH_3$, $(CH_3)_2N$—$C(O)$—$N(CH_3)_2$, $C_6H_5$—Se—$C_6H_5$, guanidine, pyridine, imidazole, N-methylimidazole, benzoxazole, benzothiazole, pyrrolidine, piperidine, piperazine, aniline, N,N-dimethylaniline, benzylamine, N-ethylbenzylamine or diphenyl sulfide.

4. Process for the preparation of organic salts of bis(perfluoroalkyl)phosphinate anions according to claim 1, wherein the alcohol employed is an aliphatic alcohol.

5. Process according to claim 1, wherein the alcohol employed is methanol, ethanol, isopropanol, n-propanol, butanol, hexanol and benzyl alcohol.

6. Process according to claim 1, wherein the alcohol employed is a fluorinated aliphatic alcohol.

7. Process according to claim 1, wherein the alcohol employed is an unsaturated alcohol.

8. Process for the preparation of organic salts of bis(perfluoroalkyl)phosphinate anions according to claim 1, wherein the tris(perfluoroalkyl)phosphine oxide employed is a tris(perfluoroalkyl)phosphine oxide in which the three perfluoroalkyl groups are identical or different.

9. Process for the preparation of organic salts of bis(perfluoroalkyl)phosphinate anions according to claim 1, wherein the tris(perfluoroalkyl)phosphine oxide employed is a tris(perfluoroalkyl)phosphine oxide in which the perfluoroalkyl groups contain 1 to 12 C atoms and are straight-chain or branched.

10. Process according to claim 8, wherein the tris(perfluoroalkyl)phosphine oxide employed is $(CF_3)_3P(O)$, $(C_2F_5)_3P(O)$, $(C_3F_7)_3P(O)$ or $(C_4F_9)_3P(O)$.

11. Process for the preparation of organic salts of bis(perfluoroalkyl)phosphinate anions according to claim 1, wherein the reaction is carried out at a temperature of $-20°$ C. to $200°$ C.

* * * * *

UNITED STATES PATENT AND TRADEMARK OFFICE
CERTIFICATE OF CORRECTION

PATENT NO.        : 7,576,242 B2
APPLICATION NO.   : 10/579555
DATED             : August 18, 2009
INVENTOR(S)       : Ignatyev et al.

It is certified that error appears in the above-identified patent and that said Letters Patent is hereby corrected as shown below:

On the title page, item (75), the second inventor reads "Urs Welz-Biermann", should read --Uwe Welz-Biermann--.

Signed and Sealed this

Twenty-seventh Day of October, 2009

David J. Kappos
*Director of the United States Patent and Trademark Office*

UNITED STATES PATENT AND TRADEMARK OFFICE
CERTIFICATE OF CORRECTION

PATENT NO. : 7,576,242 B2  
APPLICATION NO. : 10/579555  
DATED : August 18, 2009  
INVENTOR(S) : Ignatyev et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 326 days.

Signed and Sealed this

Seventh Day of September, 2010

David J. Kappos  
*Director of the United States Patent and Trademark Office*

UNITED STATES PATENT AND TRADEMARK OFFICE
CERTIFICATE OF CORRECTION

| | |
|---|---|
| PATENT NO. | : 7,576,242 B2 |
| APPLICATION NO. | : 10/579555 |
| DATED | : August 18, 2009 |
| INVENTOR(S) | : Nikolai Mykola Ignatyev et al. |

It is certified that error appears in the above-identified patent and that said Letters Patent is hereby corrected as shown below:

This certificate supersedes Certificate of Correction issued October 27, 2009. The Certificate is vacated since the name of the inventor on title page of patent is correct and printed in accordance with the record.

The second inventor name in printed patent is reinstated to read: --Urs Welz-Biermann--.

Signed and Sealed this
Ninth Day of October, 2012

David J. Kappos
*Director of the United States Patent and Trademark Office*